United States Patent
De Leval (10) Patent No.: US 9,198,747 B2
(45) Date of Patent: Dec. 1, 2015

(54) SURGICAL TECHNIQUE AND TOOLS FOR USE IN TREATMENT OF MALE URINARY INCONTINENCE

(75) Inventor: Jean De Leval, Louveigne (BE)

(73) Assignee: Universite De Liege and Centre Hospitalier Universitaire De Liege (BE)

( * ) Notice: Subject to any disclaimer, the term of this patent is extended or adjusted under 35 U.S.C. 154(b) by 937 days.

(21) Appl. No.: 11/976,801

(22) Filed: Oct. 29, 2007

(65) Prior Publication Data

US 2008/0210247 A1    Sep. 4, 2008

Related U.S. Application Data

(60) Provisional application No. 60/904,431, filed on Mar. 2, 2007.

(51) Int. Cl.
*A61F 2/00* (2006.01)
*A61B 17/06* (2006.01)
*A61B 17/00* (2006.01)

(52) U.S. Cl.
CPC .......... *A61F 2/0045* (2013.01); *A61B 17/06066* (2013.01); *A61B 17/06109* (2013.01); *A61B 2017/00805* (2013.01); *A61B 2017/061* (2013.01); *A61F 2250/0078* (2013.01)

(58) Field of Classification Search
CPC ............... A61B 2017/06066; A61B 17/06109; A61B 2017/061; A61B 2017/00805; A61B 2017/06071; A61B 2017/06076; A61B 2017/0608; A61F 2/0045; A61F 2250/0078
USPC ........ 600/29, 30, 37; 606/222, 148, 144, 223, 606/139, 185; 128/885, 869, DIG. 25; 604/8
See application file for complete search history.

(56) References Cited

U.S. PATENT DOCUMENTS

| | | | | |
|---|---|---|---|---|
| 2,008,251 | A * | 7/1935 | Hillebrand | ......... A61B 17/0469 223/102 |
| 6,911,003 | B2 * | 6/2005 | Anderson et al. | ................ 600/30 |
| 7,713,187 | B2 * | 5/2010 | Chu et al. | ......... 600/30 |
| 2004/0144395 | A1 * | 7/2004 | Evans et al. | .................... 128/885 |
| 2008/0132753 | A1 * | 6/2008 | Goddard | .......... A61B 17/06109 600/37 |
| 2010/0234681 | A1 * | 9/2010 | Knapp | ............. A61B 17/06109 600/37 |

* cited by examiner

*Primary Examiner* — Victoria J Hicks
(74) *Attorney, Agent, or Firm* — Blank Rome LLP (57) ABSTRACT

A transobturator technique was developed for treating male urinary incontinence. This approach helped to design specific instruments to pass around the ischio-pubic branches of the male pelvis from inside to outside (i.e from the suburethral space to the thigh fold). The inside-out transobturator sling technique uses specific instruments and a polypropylene mesh with two arms that are passed inside to outside through the obturator foramens, pulled for compressing the bulbar urethra upward, and tied to each other across the midline. The mesh passes around the ischio-pubic branch before being tied under the bulbar urethra where it brings tension and support.

15 Claims, 11 Drawing Sheets

FIG. 1Ci  FIG. 1Cii  FIG. 1Ciii

SURGICAL TECHNIQUE AND TOOLS FOR USE IN TREATMENT OF MALE URINARY INCONTINENCE

This application is a complete application which claims priority from and the benefit of U.S. Provisional Application Ser. No. 60/904,431, filed Mar. 2, 2007.

FIELD OF THE INVENTION

The following surgical procedure concerns urology; and especially the treatment of male post-operative urinary incontinence; a condition that mainly occurs after prostate surgery.

BACKGROUND OF THE INVENTION

Prostate cancer (PCs) represents about 30% of all cancers in men. For more than twenty years the wide use of biologic markers and screening campaigns have contributed to detection of the disease (PCs) at early stages, hence, aiming to improving the cure rates. This goal could be reached either by surgical removal of the gland (radical prostatectomy), radiation therapy or focused ultrasounds. Nonetheless, incontinence rates after these therapies are far from anecdotal. The literature reports an incidence of 5 to 45% of incontinence after radical prostatectomy and up to 7% of cases after external beam radiation therapy (EBRT). Furthermore, the surgery for benign adenoma such as transurethral resection or open enucleation also carries a certain risk of incontinence (about 1.9% of incidence).

Male stress urinary incontinence (SUI) that occurs as a result of sphincter dysfunction after radical prostatectomy is a devastating adverse event for patients and a frustrating problem for urologists. The incidence of this clinical condition ranges between 3% and 45%. Initial management is usually conservative and includes the use of diapers or pads, penile clamps, or various collecting systems (e.g. condom catheter). Mild degrees of SUI in the early postoperative period may be improved by pelvic muscles exercises, physiotherapy, and pharmacotherapy.

When these therapies fail to alleviate SUI, patients are usually offered one of the following surgical alternatives: bulking agent infections, artificial urinary sphincter (AUS) placement or sling insertion. Urethral or bladder neck balloon compression devices have also been reported by a few groups. Transurethral injections of various bulking materials have been used for decades and are minimally invasive, safe and well tolerated. Nevertheless, effectiveness is usually temporary, requiring multiple injections, and long-term results have been disappointing so far, with cure rates achieving only 20-40%.

Pioneered by Foley 50 years ago and largely developed by Scott in the early 1970s, the AUS has culminated in the hydraulic AMS-800 final version commercialized by American Medical Systems. Currently, the AUS remains the current gold standard of treatment for post-prostatectomy incontinence. Numerous reports with medium- to long-term followup of this procedure exist in the literature, with 61% to 96% success rates as defined by variable criteria. The results are generally lower among patients with radiation-induced or -associated incontinence.

Despite its attractiveness, the AUS is an expensive mechanical device that can fail and requires manual opening to empty the bladder and therefore dexterity and/or mental capacity to use the device. In addition, surgical revision or replacement may be required due to mechanical failure, infection or cuff erosion. The 5-year reoperation rate has been reported to range between 17% to 57%.

Sling procedures are conceptually attractive in that they are inexpensive, nonmechanical and allow for physiological voiding without significant obstruction. The use of fixed urethral compression for the treatment of male SUI began in 1961 with Berry who utilized acrylic prostheses to compress the ventral urethra against the urogenital diaphragm and was followed by the different sling procedures developed by Kaufman in the 1970s. Since then, various techniques of bulbar urethra compression using synthetic and/or biologic materials have emerged.

Sling devices are usually secured either over the rectus abdominalis fascia/muscles after retropubic passage, or at each inferior pubic ramus with the use of bone screws in order to avoid a separate suprapubic incision. Results from clinical series assessing the intermediate- and long-term outcome of sling procedures indicate that success rates may compare favorably with those obtained after AUS placement. Yet, no randomized study comparing the results of both procedures are currently available.

Even though in the majority of cases urine leakage will disappear within the year, about 10% of patients (from 5 to 45% in the literature) will require permanent pad wearing or any other protection system after this time span. Thus, a number of devices have been invented to reduce the social impact of incontinence. Besides the external systems (penile clamp, collecting bags, incontinence pads, etc.) surgically implanted materials have also emerged.

Periurethral injections have been developed for decades. Different materials have been used: collagen, Macroplastique®, autologous fat, Deflux®, but results are disappointing. And cure rates roughly reach 40%. Surgical urethral compression has been used since 1961, at first with acrylic prostheses designed by BERRY. Later, in 1968 KAUFFMAN invented an inflatable silicone prosthesis with polytetrafluoethylene fasteners.

Since then, different techniques of bulbar compression have emerged. Materials used are synthetic, biologic or both. A variety of anchorage systems are utilized: from retropubic passage with fixation to rectus abdominis muscles to bone anchorage to ischio pubic branches or passage into the obturator foramens. Some authors suggest peroperative multichannels urodynamic studies to improve the results.

SUMMARY OF THE INVENTION

To avoid any blind dissection of the pelvic space that carries the risk of bladder, bowel or vascular trauma; or the bone anchorage that could be either painful or infection bearing, a transobturator technique was developed. The feasibility study of the surgical procedure has been conducted on cadavers. This approach helped to design specific instruments to pass around the ischio-pubic branches of the male pelvis from inside to outside (i.e from the suburethral space to the thigh fold).

Very few publications on the transobturator technique are described in the literature. For instance, only Bauer underlines a passage from inside to outside but does not give any description of the surgical tools.

The inside-out transobturator sling technique of the present invention uses specific instruments and a polypropylene mesh with two arms that are passed inside to outside through the obturator foramens, pulled for compressing the bulbar urethra upward, and tied to each other across the midline. Cure was defined by no pad use and improvement by a number of pads/d<2 and reduced by at least 50%.

Anatomic differences between male and female do not allow the use of the same instruments from one to another. Among these differences, the followings are the most important to the present invention.

Pelvic bones in males are thicker than in females.

The distance between ischio-pubic branches is wider in females.

The trajectory of the mesh, though identical at its proximal segment in both genders, diverges when reaching the thigh fold.

Conversely to the tension-free technique in treatment of female stress urinary incontinence as described in my prior U.S. Pat. No. 7,204,802, hereby incorporated in its entirety by reference, in males the mesh of the present invention passes around the ischio-pubic branch before being tied under the bulbar urethra where it brings tension and support. The tying of both arms of the mesh prevents the use of screws or any other bone anchorage system.

The surgical procedure utilizes specifically designed instruments allowing, via an inside-out transobturator approach, placement of a compressive polypropylene mesh at the level of the bulbar urethra. The designed instruments include a pair of helical passers, a guide and a specifically-shaped synthetic mesh.

In case of associated urethral stenosis, classic endoscopic urethrotomy is performed first. Antibiotic prophylaxis was systematically carried out by intravenous administration of third-generation cephalosporin.

The instruments used for the inside-out transobturator sling procedure of the present invention include passers which are pairs of stainless steel instruments that are specific for the left and right sides. They comprise a handle, a vertical segment, and a flat curved segment ending with a conic section formed by curled segments that enable the intraoperative attachment of a hollow polyethylene tube. The flat curved segment is perpendicular to the handle's axis and comprises three segments: a proximal, linear segment, an intermediate, open circular segment with a 3 cm radius, and a terminal, open circular segment having a shorter radius and ending with a conic section formed by curled segments that enable the intra-operative attachment of a hollow polyethylene tube. As detailed below, the hollow plastic tubes are used to ease the passage of each arm of the mesh through the obturator foramens.

Another tool used is a guide which is a stainless steel device including a semi-circular gutter with a blunt end and with a 'bayonet' shape intended to avoid any traumatic compression of the bulbous urethra during insertion of the passers. It is intended to act both as a shoe-horn for slipping in each passer alongside the gutter and as a barrier for preventing entry of the passers into the pelvic cavity. Its proximal portion bears two small wings that are parallel to the gutter's plane, and serve for holding the device.

A monofilament, macroporous, low density polypropylene mesh (Gynemesh PS®, Ethicon, Somerville, N.J., USA) is cut in the operating theater according to a preset frame. The mesh comprises a central portion that is 3 cm large and having two lateral arms. Its ventral extremity is linear while its dorsal end is rounded. The mesh bears the two lateral arms that arise mainly from the dorsal aspect of the mesh. The width of the proximal portion of each arm progressively decreases from 4 cm to 2 cm over a 2.5 cm distance.

The specific instruments have been designed enabling the two mesh lateral arms to be I) easily passed around the inferior pubic rami, ii) pulled downward for compressing the bulbar urethra upward, and iii) tied to each other for maintaining sling tension. The inside-out transobturator approach for male sling insertion bears a minimal risk of harming any sensitive structure in the male pelvis. For the purpose of circumventing the inferior pubic rami, an inside-out route is used, as compared with an outside-in one, which carries a lower risk of penetrating the pelvic space.

The transobturator approach minimizes the risk of bladder, bowel, and vessel injuries, which can be observed during a blind, retropubic passage of a needle through the pelvic space—particularly in post-radical prostatectomy patients. In addition, this approach allows for avoidance of bone anchors and related issues including osseous infection and pain. The transobturator sling for treating male SUI of the present invention allows to tie up the two transobturator mesh arms to each other, thus preventing any risk of mesh 'slippage'.

The inside-out transobturator sling includes a mesh having two lateral arms that are initially passed from either side of the urethral bulb through the obturator foramens, then rotated around the inferior pubic rami, and finally pulled and bound to each other across the midline so that the central portion of the mesh exerts an upward bulbar urethra compression.

After installation of the patient in a lithotomy position, legs on stirrups, with thighs in hyperflexion (110° angle) and slight abduction, the surgical area is prepared and draped in a sterile fashion. A 16-F Foley's catheter is inserted and the scrotal skin is temporarily pulled upwards with two stitches fixed at the inner side of both thighs, in order to facilitate access to the perineum. A 6 cm sagittal skin incision is made at the median raphe of the perineum ending 2 cm above the anal margin.

Transsection of the subcutaneous fat and Colle's superficial perineal fascia allows to gain access to the bulbospongious muscle, which is freed ventrally to the pubic symphysis and dorsally to the central body of the perineum. Further dissection is conducted laterally to expose the ischiocavemous muscles.

Together with the transverse muscles, the bulbospongious and ischiocavemous muscles delineate, on either side of the urethral bulb, a triangular space. The inferior layer of the median perineal aponeurosis, which is located in depth at this space, is carefully dissected. Cautious hemostasis of the small perforating vessels of the urethral bulb is done by electrocauterisation.

Starting with the right side, the bulbar urethra is reflected on the left side using a retractor, thus providing access to the median perineal plane. Metzenbaum scissors are used to open up the inferior layer of the median perineal aponeurosis in the anterior portion of the triangular space, just lateral to the bulb. Scissors transect the muscular plane and then perforate the upper layer of the median perineal aponeurosis.

The guide is inserted through the scissors-initiated dissection path with a 45° angle relative to the urethral sagittal plane in order to come into contact with the upper part of the ischiopubic branch. The guide is introduced further and perforates the right internus obturator muscle and obturator membrane. The open side of the guide must be facing the operator.

The distal linear segment of the passer is slipped along the gutter of the guide so as to pass through the obturator membrane. The guide is removed and, thanks to a rotational movement of the passer's handle, the tip of the passer appears at the outer edge of the ischiopubic ramus, at its junction with the body of pubis.

A hollow plastic tube is attached to the tip of the passer and the device assembled with the tube is rotated backward The plastic tube becomes externalized at the perineal level and is subsequently freed from its supporting passer. At this stage, the tube bridges the perineum with the right outer aspect of the obturator foramen. The same technique, using the left passer and a second plastic tube, is applied to the left side.

The dorsal extremity of the mesh is attached to the central body of the perineum using a 2/0 non-absorbable suture. A nylon wire is passed through the tip of the left arm of the mesh; both ends of the wire are introduced into the left hollow tube (at the perineal level).

By pulling on both wire ends (at the external obturator level), the left arm of the mesh is attracted into the tube. Pulling of the wire is stopped just before the proximal, larger portion of the arm enters the tube. Hemostatic forceps are used to grasp and lock the wire's ends at their exit from the tube and the same manoeuver is applied to the right arm of the mesh. The most ventral portion of the mesh is then fixed to the aponeurosis of the ischiocavernous muscles by one separate stitch of 2/0 non-absorbable suture to either lateral side of the mesh. Unfolding of the mesh is achieved by slightly pulling on the plastic tubes; the mesh then appears to cover the bulbous urethra.

At this stage, a urodynamic evaluation is performed and the bladder is filled with 300 mL of normal saline. Thanks to a dual channel urodynamic urethral catheter, the urethral pressure profile (UPP) is recorded and the abdominal leak point pressure (ALPP) and maximal urethral pressure (MUP) are measured.

The nylon wires and plastic tubes are grasped on either side and pulled towards the operator, thus attracting both the mesh and the urethral bulb cranially. The tubes and then the wires are removed and both arms of the mesh are crossed and temporarily bound to each other with forceps over the bulb. Urodynamic measurements are repeated until tension on both arms of the mesh increases ALPP to approximately 100 cm $H_2O$.

At this stage, the two arms of the mesh are tied to each other by a triple knot; the latter is sutured to the mesh covering the urethral bulb and excess arm ends are cut off. The urodynamic urethral catheter is removed and the Foley catheter is reintroduced into the bladder. Insertion of the catheter should be easy, ideally without resistance. Hemostasis is completed when necessary, and the different tissue layers (Colle's fascia, subcutaneous fat, and skin) are closed plane by plane using polyglactin suture.

These and other objects of the invention, as well as many of the intended advantages thereof, will become more readily apparent when reference is made to the following description taken in conjunction with the accompanying drawings.

BRIEF DESCRIPTION OF THE DRAWINGS

The following drawings illustrate examples of various components of the surgical technique and tools for use in treatment of male urinary incontinence disclosed herein, and are for illustrative purposes only. Other embodiments that are substantially similar can use other components that have a different appearance.

FIGS. 1Ci, 1Cii and 1Ciii illustrate alternate tip endings of the spiral section of the surgical passer.

FIGS. 3 through 14A illustrate the progressive surgical steps in performing the surgical technique for treating male urinary incontinence of the present invention.

DETAILED DESCRIPTION OF THE PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

The Passer

Figure 1:
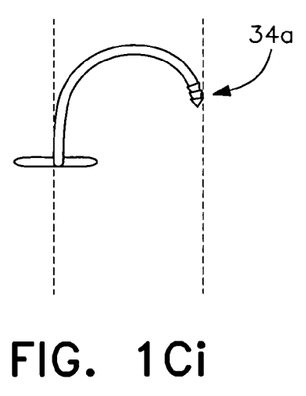
Figure 1A:
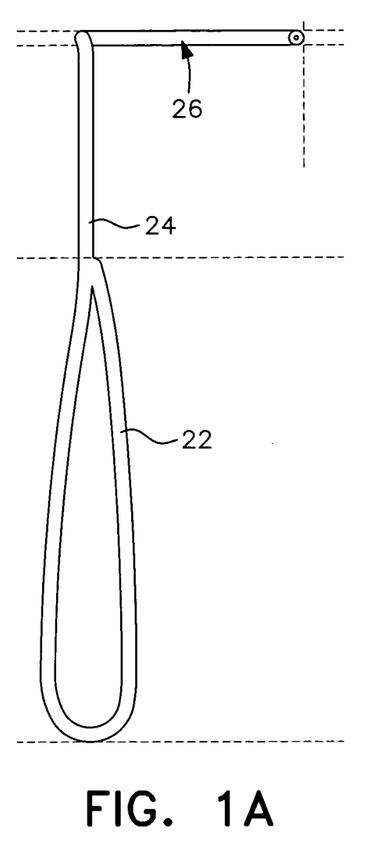
FIG. 1A is a side view of the surgical passer used for treating male urinary incontinence.
Figure 1B:
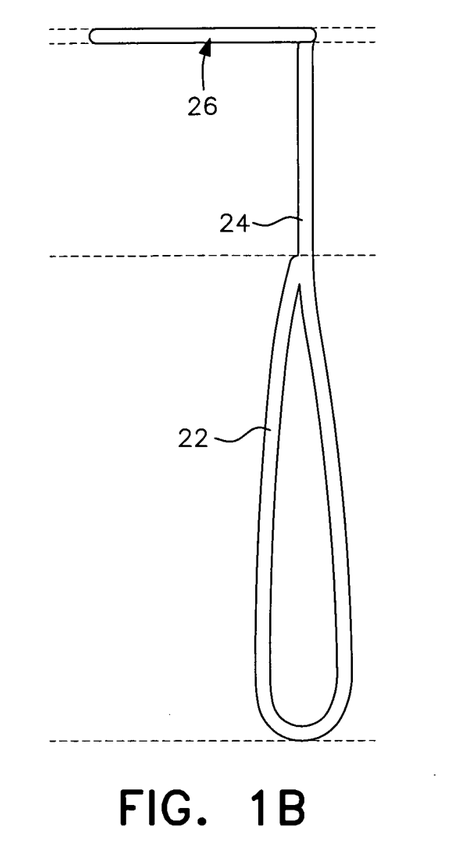
FIG. 1B is an opposite side view of the surgical passer.
Figure 1C:
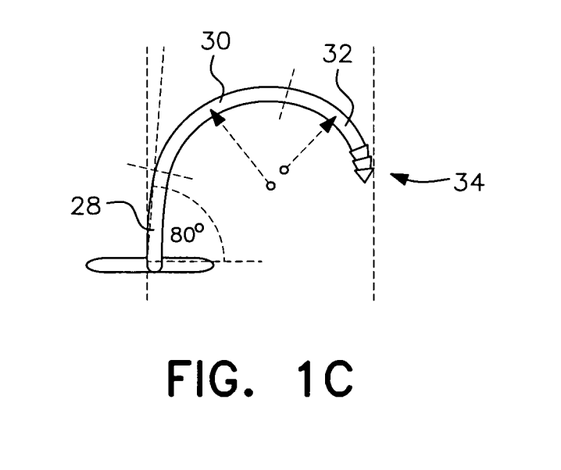
FIG. 1C is a top plan view illustrating the four parts of the spiral section of the surgical passer.

As shown in FIGS. 1A, 1B and 1C, each helical passer is made of three parts: a handle 22, a vertical segment 24 and a horizontal segment 26 formed in a spiral.

The handle 22 has a height of 8 to 15 cm. It can be either made of stainless steel or any other material such as plastic.

The vertical segment 24 measures from 2 to 6 cm; preferably 4 cm, with a diameter of 2.5 to 4.5 mm in section. It can also be made of stainless steel. It can either be connected to the handle unless it is formed integrally as one piece.

The segment 26 is spirally shaped in a horizontal plane, perpendicular to the vertical segment 24. Segment 26 measures 6 to 10 cm—preferably 8.5, with a diameter of 2.5 to 4.5 mm in section. It is also made of stainless steel. The spiral is divided into four parts as shown in FIG. 1C. The first part 28 is a 2-cm long linear segment which makes a 10° angle with the sagittal plane of the vertical segment 26. The second part 30 is a 4-cm long, circular segment of a circle of 3-cm of radius. The third part 32 is a 2.5-cm long, circular segment of a circle of 1.6-cm of radius. The fourth part 34 is the tip that can have three different shapes. Segment 34a is a ½ cm conic segment formed by three curled segments enabling the attachment of a tube ('tube-passing' needle) (FIG. 1Ci). Segment 34b is an eyelet of 0.5 to 1.5 mm through which a string is passed ('stringpassing' needle) (FIG. 1Cii). In segment 34c, the very end of the tip is flat and is 5-mm shorter. This spiral of 1.5 to 3.5 mm of diameter can receive a hollow tube whose distal end is sharply pointed and measures 5 mm ('tube-supporting' needle) (FIG. 1Ciii).

The Guide

Figure 2A:
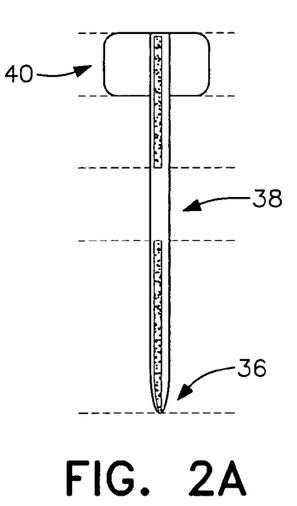
FIG. 2A is a front view of a guide for the surgical passer of the present invention.
Figure 2B:
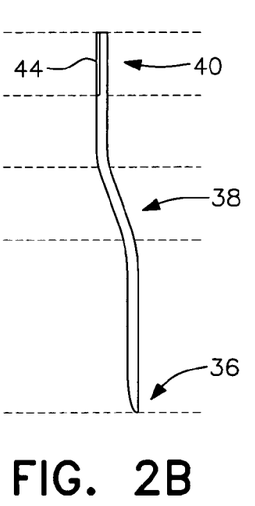
FIG. 2B is a side view of the guide.
Figure 2C:
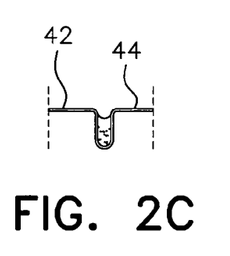
FIG. 2C is a top view looking down initially on the tip and continuing in a direction towards the wings forming the handle of the guide.

The "introducer" or "guide" as shown in FIGS. 2A, 2B and 2C is an 8 to 12-cm long instrument with a semi-cylindrical hollow gutter of a 3 to 5-mm diameter. It is made of stainless steel, and has a blunt atraumatic tip 36. The body 38 of the introducer is not straight right but wiggles on its center creating a distance one centimeter between the proximal and the distal ends. This particular shape is intended to prevent any important compression of the bulbar urethra during the procedure. In addition the proximal extremity 40 of the guide is winged 42, 44 to serve as the handle. The accurate guide or introducer acts as a shoehorn to avoid any intrusion into the pelvis during the procedure.

The Mesh

Figure 2D:
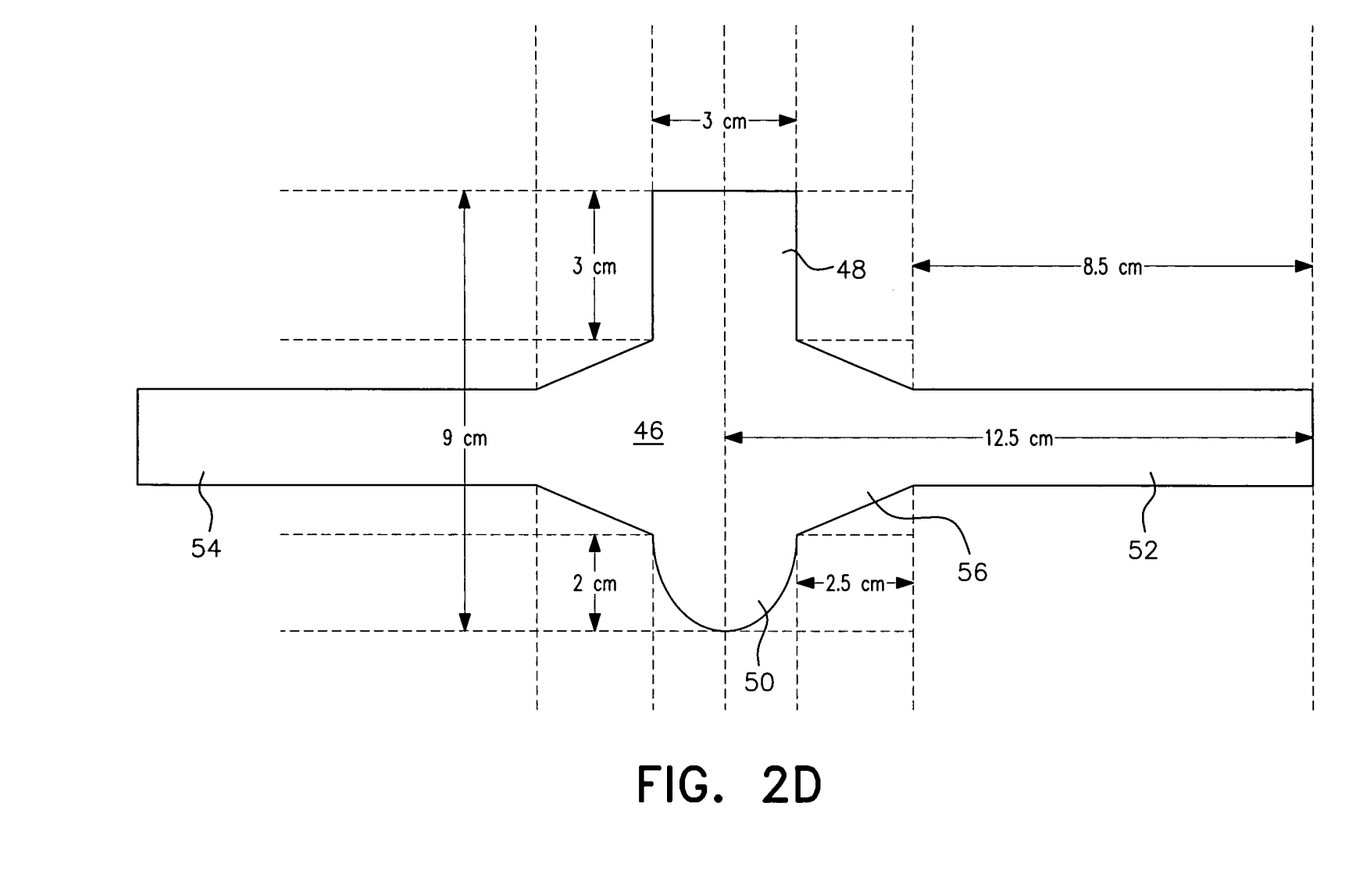
FIG. 2D is a plan view of the mesh support structure introduced by the surgical technique of the present invention for treating male urinary incontinence.

The mesh shown in FIG. 2D is made of synthetic material preferably low density polypropylene. It can be either cut or shaped in the operating room from a proper metallic frame or be included in a ready to use set. The prosthesis comprises a central part 46 of 5 to 10-cm long and 2 to 5-cm in width. Its anterior end 48 is linear but the posterior extremity 50 is rounded. The mesh is laterally prolonged by two lateral arms 52, 54 of 10 to 15 cm in length. The width of the lateral arm progressively decreases at 56 in a distance of 2 to 4 cm, from 4 cm to 2 cm. Thus the latter segment measures from 8 to 13 cm. The arms 52, 54 of the mesh do not arise from the middle of the prosthesis but are more posterior.

The Surgical Procedure

Additional materials to those aforementioned include two polyethylene hollow tubes. These tubes have from 25 to 40 cm of length with an outer diameter of 3.8 to 4.6 mm. The inner diameter measures from 2.8 to 3.8 mm. Two nylon guide wires are used of 60 to 100 cm long, and 0.5 to 1.3 mm in section.

The surgical procedure can be carried out under general or spinal anaesthesia. And antibioprophylaxis is achieved by per-operative intravenous administration of 2 g of a third generation cephalosporin.

Figure 3:
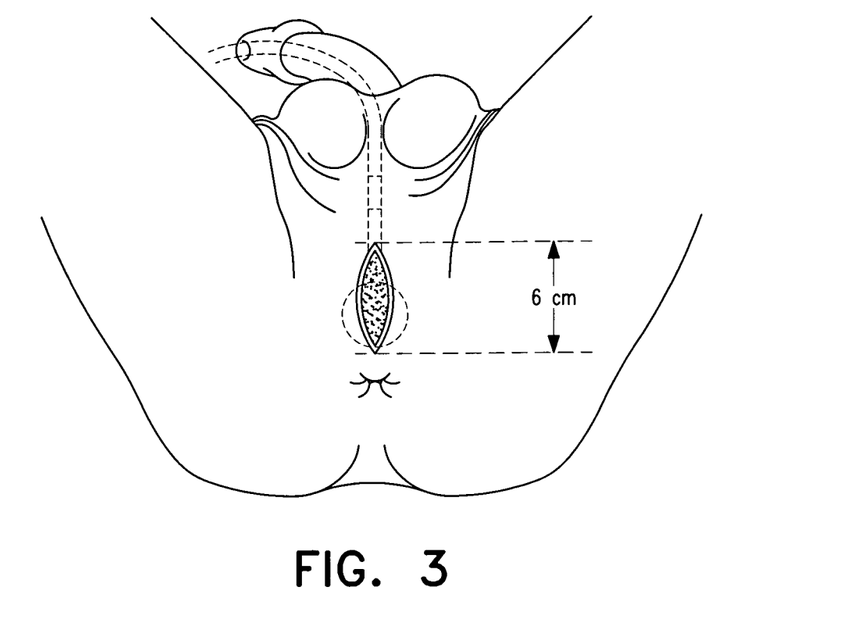

The patient is installed in gynecologic position; thighs are put in hyper flexion up to 110° with an additional slight abduction as shown in FIGS. 3 through 14. Sterile draping of the operative field is achieved after proper cleansing of the perineum up to the hypogastric region with a standard antiseptic solution. Care is taken to maintain an easy access to the penis and the perineum all along when surgery proceeds. A 16-French Foley catheter is inserted first. Afterwards the scrotum is temporarily suspended by stitches on both inner thighs to improve the access of the perineum. Then a 6-cm long median incision is performed from behind the scrotum as it stops 2-cm away from the anal margin. And dissection of subcutaneous fatty tissue reveals Colle's fascia (FIG. 3). Transaction of Colle's fascia reveals the bulbo spongious muscle. Thereafter the bulbo spongious muscle is dissected upwards to the pubic symphysis and downwards to the central body of the perineum. Dissection is then conducted laterally to the ischio cavernous muscles. These muscles-ischio cavernous and bulbo cavernous-limit a triangular space which dissection gives access to the median perineal aponeurosis. At that stage, it is reminded that the important blood vessels and nerves run along the inner aspect of ischio cavernous muscles. Cautious hemostasis of small perforating vessels is realized by the electrocautery.

The specifically designed helical passers shown in FIGS. 1A through 1C are then used to turn around ischio pubic branches from inside to outside. The passers allow the introduction of the hollow plastic tubes from outside to inside. Finally the arms the mesh can traverse the obturator foramens guided through the hollow tubes.

Figure 4:
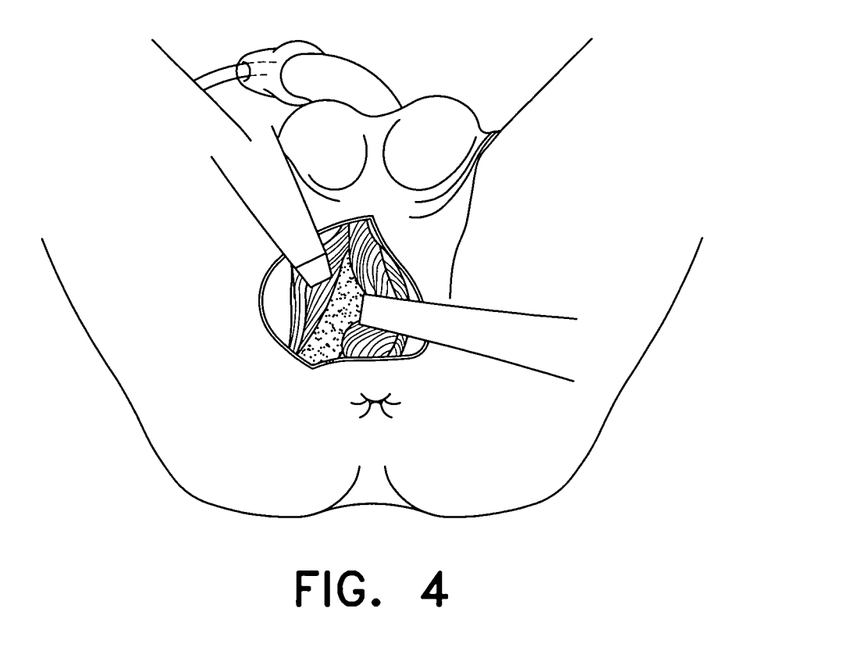
Figure 5:
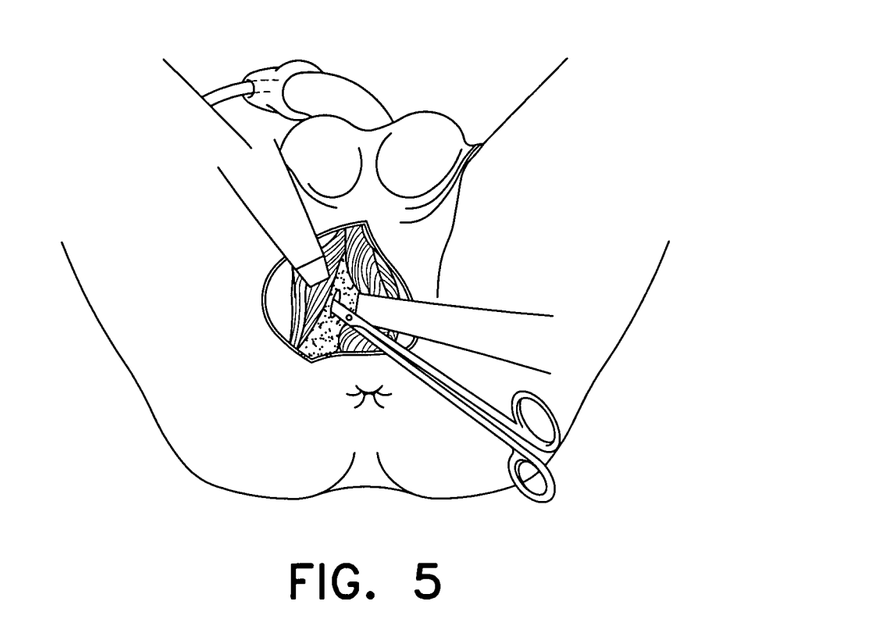
Figure 6:
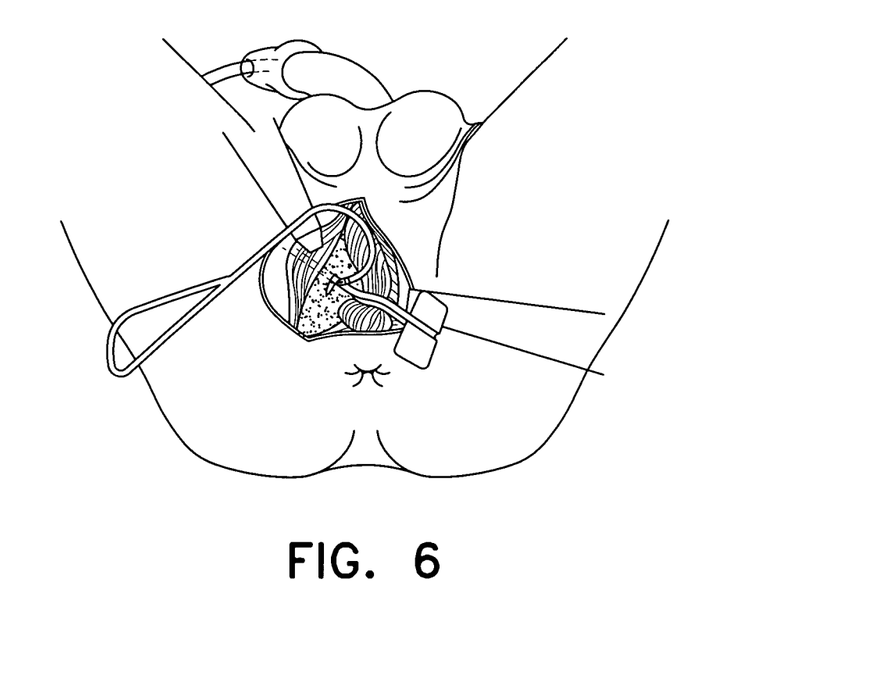
Figure 7:
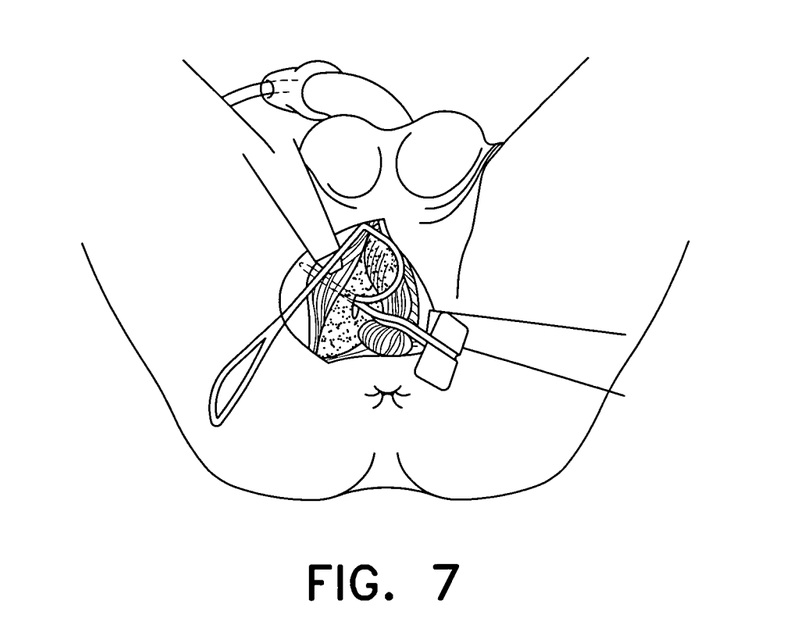
Figure 8:
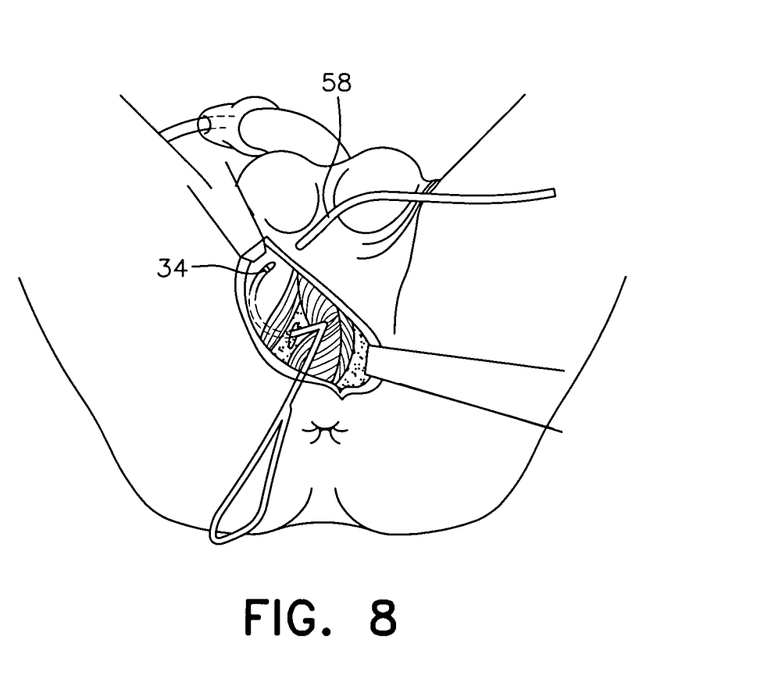
Figure 9:
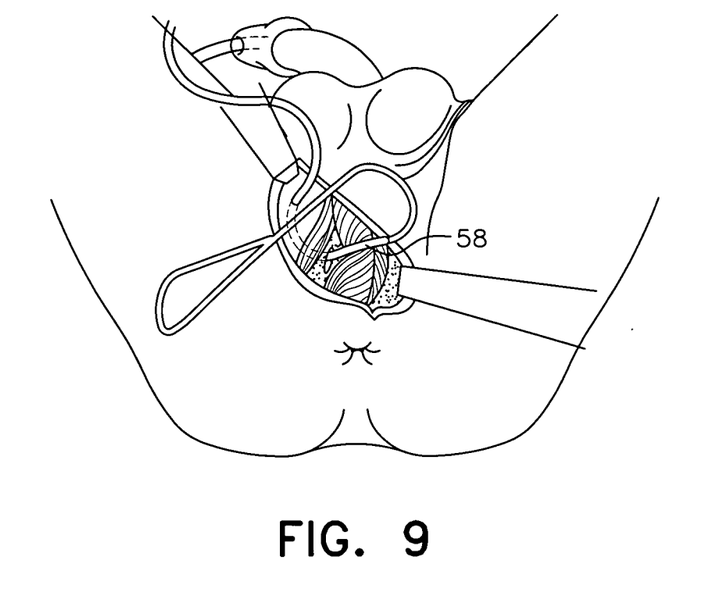

The right side is started first. The bulbar urethra is reclined on the left side using a Faraboeuf retractor; thus giving sight to the median perineal plane (FIG. 4). Then Metzebaum scissors are used to open up the median perineal aponeurosis. The incision goes from the upper part of the triangular space to the lateral edge of the bulb. Scissors transect the muscular plane before perforating the upper aspect of the median perineal aponeurosis (FIG. 5). Then the guide is inserted through that plane with a 45° angle to come in contact with the upper aspect of the ischio pubic branch. The blunt tip of the guide is then used to pass through both the internal obturator muscle and the obturator membrane (FIG. 6). Afterwards the helical passer is slid into the gutter of the guide to perforate the obturator membrane (FIG. 7-8). At that time the guide is removed and a rotation movement going forwards is applied to the passer as its distal end 34 appears at the junction between the ischio pubic branch and the pubic bone (FIG. 8). The 30-cm long hollow plastic tube 58 is then clipped on the extremity of the passer and the device is rotated backwards. At that time the tube bridges the median perineal incision and the upper aspect the ischio pubic branch (FIG. 9). Thereafter the same procedure is also conducted on the opposite side.

Figure 10A:
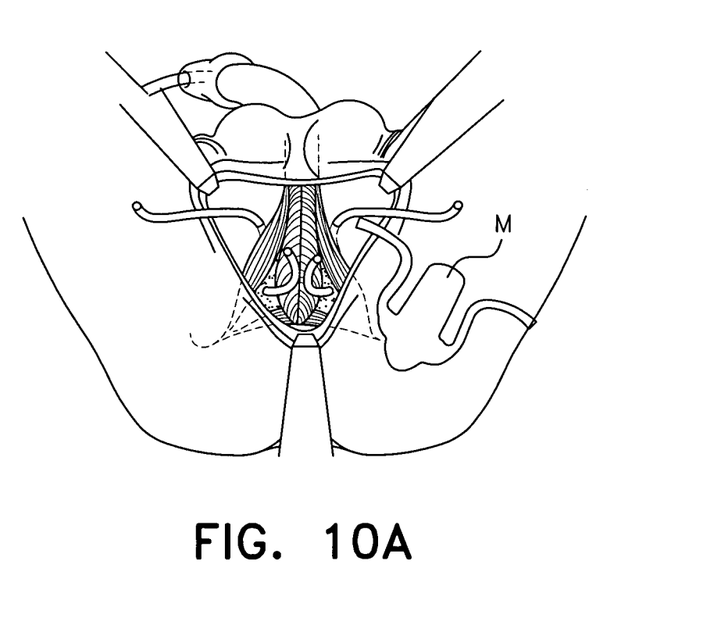
Figure 10B:
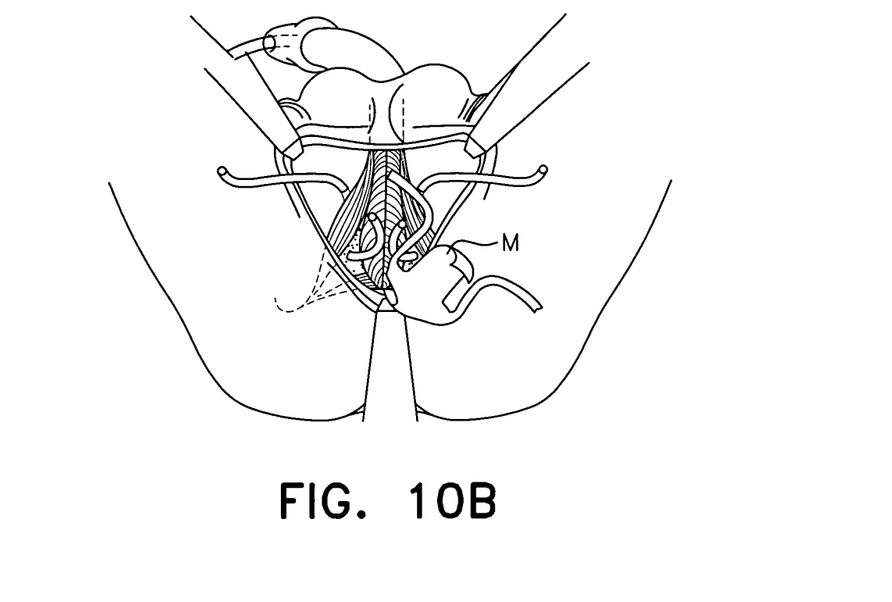
Figure 11:
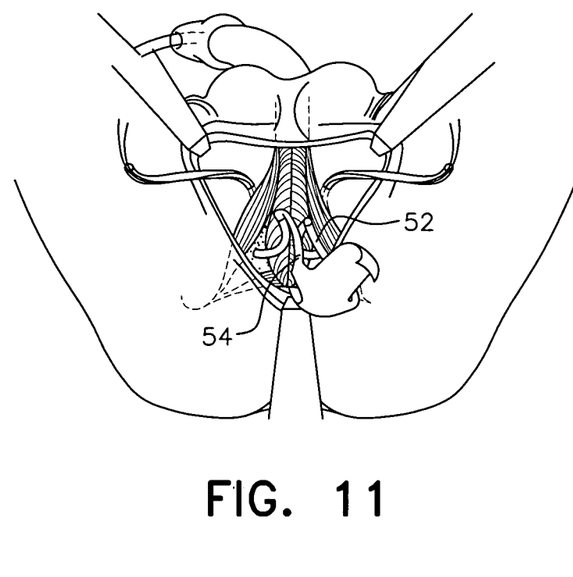
Figure 11A:
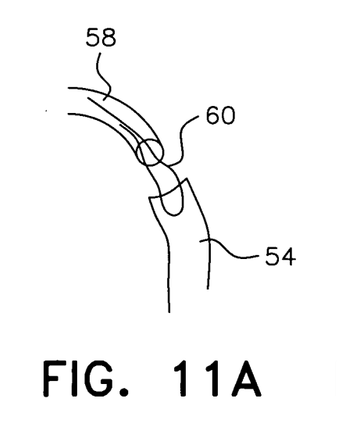
Figure 11B:
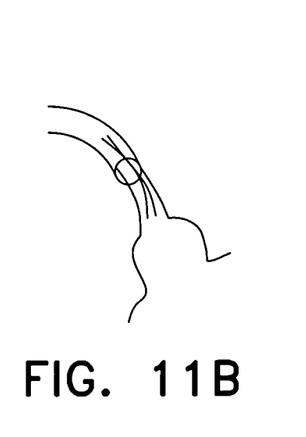
Figure 11C:
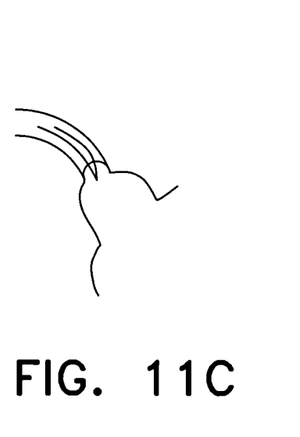
Figure 12:
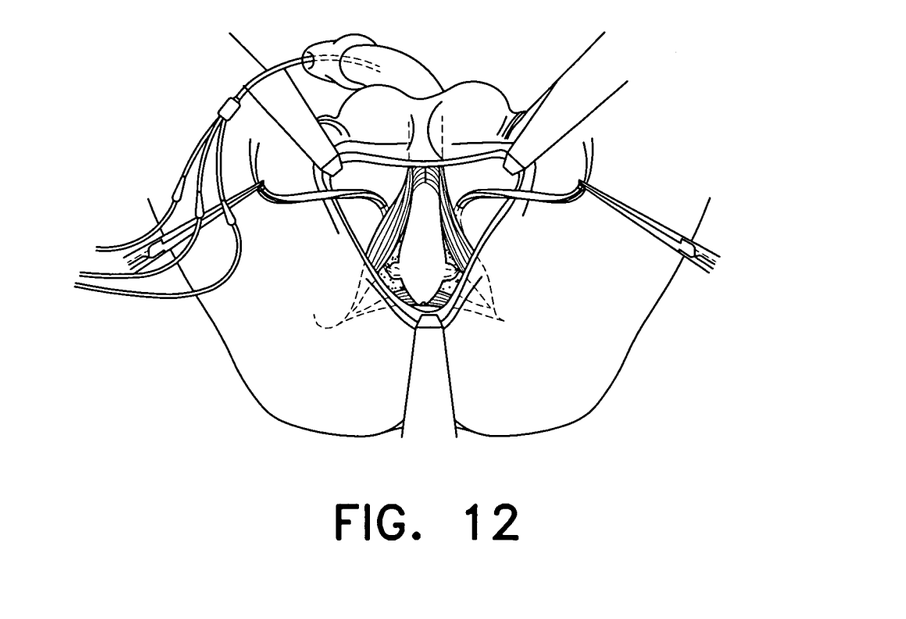

The proximal extremity of the mesh (M) is brought in contact with the bulb (FIG. 10A). Then this rounded extremity of the mesh fixed with a 2/0 non-absorbable sutures (Mersuture©) to the central body of the perineum (FIG. 10B). The nylon guide wires 60 are then attached to the arm of the mesh and altogether passed throughout the tube until it reaches the larger part (the 2 to 4-cm long proximal part)(FIG. 11A, 11B, 11C). A Christophe grip is used to temporarily fasten the plastic tube and the mesh together. The same procedure is then conducted on the opposite side (FIGS. 11-12). Afterwards the anterior part of the mesh is fixed with two stitches of 2/0 non-absorbable suture to the aponeurosis of ischio cavernous muscles (FIG. 12). A slight tension on the guide wire unfolds the mesh.

To perform a multi channel urodynamic study, the bladder is filled with 300 mL of saline. The urodynamic urethral catheter assesses an initial abdominal leak point pressure (ALPP) and a maximal closure pressure (PCM).

Figure 13:
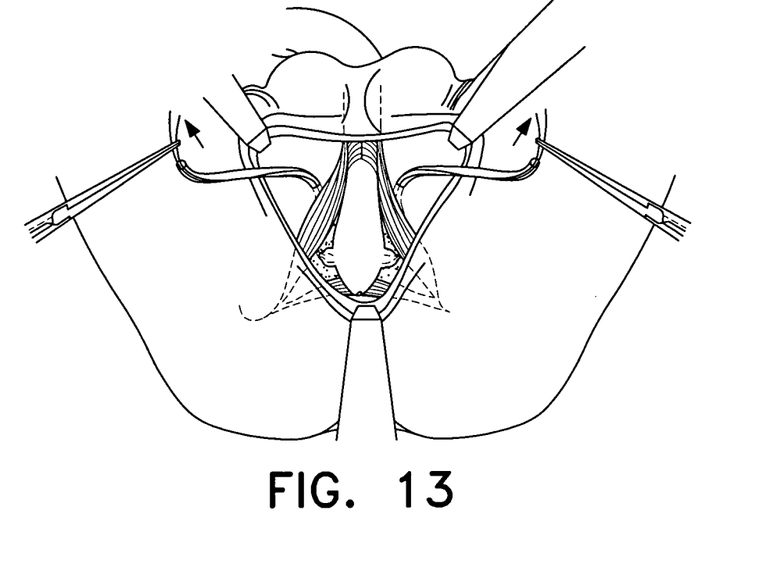
Figure 13A:
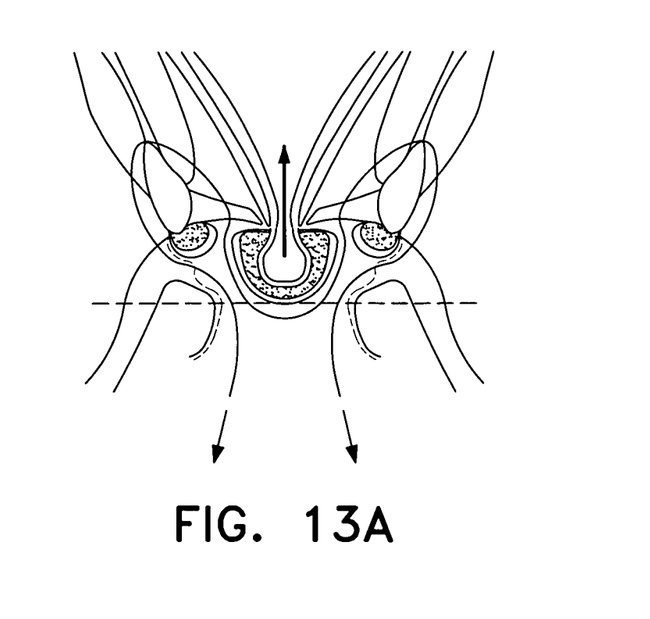
Figure 13B:
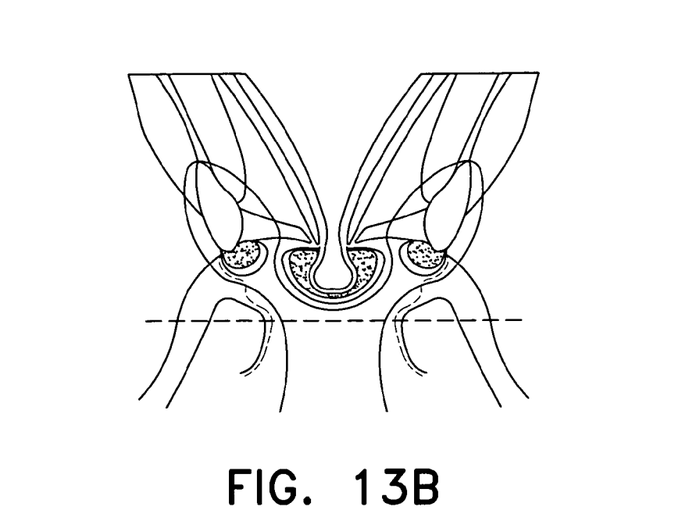
Figure 14:
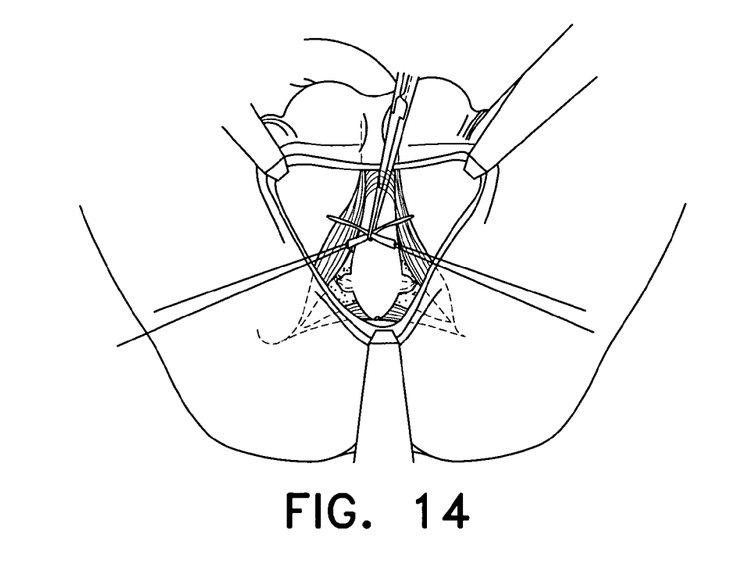
Figure 14A:
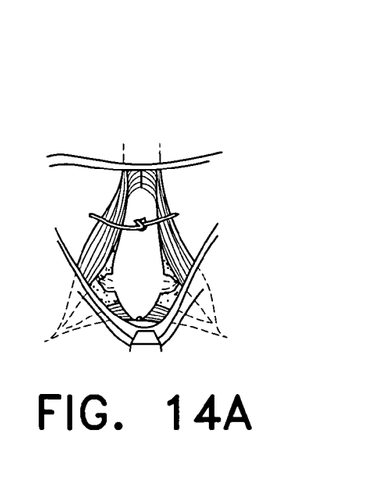

By pulling on both arms 52, 54 of the mesh the bulbar urethra is compressed upwards (FIG. 13, 13A, 13B). The plastic tubes and the nylon guides are then removed and the arms of the mesh are temporarily crossed under the bulb (FIG. 14) until the leak pressure is heightened to 60 or 120 cm of water. Finally the arms of the mesh are definitely knitted (FIG. 14A). The 16-French Foley catheter is inserted back, ideally without any resistance. Closure of the tissues is realized step by step.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A surgical passer for use in treating male urinary incontinence, said surgical passer comprising:
   a handle;
   a segment having two ends, one end of the segment extending from said handle; and
   a spiral section having two ends and a length, one end of the spiral section extending from another end of said segment, said spiral section further including:
   a first part of said spiral section extending from said segment and being a linear part having a length of between 1/5 and 1/3 the length of said spiral section,
   a second part of said spiral section extending from said first part of said spiral section and being a circular part,
   a third part of said spiral section extending from said second part of said spiral section and being a circular part having a radius less than a radius of said second part of said spiral section, and
   a fourth part of said spiral section extending from said third part of said spiral section, said fourth part of said spiral section terminating in a free end,
   said spiral section extending in a common horizontal plane perpendicular to said segment.

2. The surgical passer for use in treating male urinary incontinence as claimed in claim 1, wherein said segment measures 6 to 10 cm and has a diameter of 2.5 to 4.5 mm.

3. The surgical passer for use in treating male urinary incontinence as claimed in claim 2, wherein said second part of said spiral section has a radius of 3 cm.

4. The surgical passer for use in treating male urinary incontinence as claimed in claim 3, wherein said third part of said spiral section has a radius of 1.6 cm.

5. The surgical passer for use in treating male urinary incontinence as claimed in claim 2, wherein said first part of said spiral section is 2 cm long and makes a 10° angle with a sagittal plane of said segment.

6. The surgical passer for use in treating male urinary incontinence as claimed in claim 1, wherein at least said segment and said spiral section are stainless steel.

7. The surgical passer for use in treating male urinary incontinence as claimed in claim 1, wherein said free end has three curled segments.

8. The surgical passer for use in treating male urinary incontinence as claimed in claim 1, wherein said free end includes an eyelet.

9. The surgical passer for use in treating male urinary incontinence as claimed in claim 1, wherein said handle is integral with said segment.

10. A surgical passer for use in treating male urinary incontinence, said surgical passer comprising:
a handle;
a linear segment having a first end and a second end, said first end of said linear segment connected to and extending from said handle; and
a spiral section having a length connected to and extending from said second end of said linear segment, said spiral section extending in a common horizontal plane perpendicular to said linear segment, said spiral section including:
a first part having, a linear shape having a length of between ⅕ and ⅓ the length of the spiral section,
a second part of said spiral section extending from said first part of said spiral section, said second part being a circular part having a radius,
a third part of said spiral section extending from said second part of said spiral section, said third part being a circular part with a radius less than a radius of said second part of said spiral section, and
a fourth part of said spiral section extending from said third part of said spiral section, said fourth part terminating in a free end having a flat tip.

11. The surgical passer for use in treating male urinary incontinence of claim 10, wherein at least said linear segment and said spiral section are stainless steel.

12. The surgical passer of claim 10, further comprising a hollow tube having a distal end that is sharply pointed.

13. A surgical passer for use in treating male urinary incontinence, said surgical passer comprising:
a handle;
a linear segment having a first end and a second end, said first end of said linear segment connected to and extending from said handle; and
a spiral section having a length connected to and extending from said second end of said linear segment, said spiral section extending in a common horizontal plane perpendicular to said linear segment, said spiral section including:
a first part having a linear shape having a length of between ⅕ and ⅓ the length of the spiral section,
a second part connected to and extending from said first part of said spiral section and having a first circular shape with a first radius,
a third part connected to and extending from said second part of said spiral section and having a second circular shape with a second radius, wherein said second radius is less than said first radius, and
a fourth part connected to and extending from said third part of said spiral section, said fourth part terminating in a free end having three curled segments.

14. The surgical passer for use in treating male urinary incontinence of claim 13, wherein at least said linear segment and said spiral section are stainless steel.

15. A surgical passer for use in treating male urinary incontinence, said surgical passer comprising:
a handle;
a straight segment having two ends, one end of said straight segment extending from said handle; and
a spiral section having two ends and a length, one end of the spiral section adjoining another end of said straight segment,
wherein a first part of the spiral section extending from said straight segment being a linear part and having a length of between ⅕ and ⅓ the length of the spiral section, a second part of the spiral section extending from said first part of said spiral section being a circular part, a third part of said spiral section extending from said second part of said spiral section being a circular part having a radius less than a radius of said second part of said spiral section, and a fourth part of said spiral section extending from said third part of said spiral section, said fourth part terminating in a free end, wherein said spiral section extends in a common plane perpendicular to said straight segment.

\* \* \* \* \*